United States Patent
Jomuta et al.

(10) Patent No.: US 10,975,053 B2
(45) Date of Patent: Apr. 13, 2021

(54) PRODUCTION METHODS FOR 1,3-DIOXOLANE COMPOUND AND PERFLUORO(2,2-DIMETHYL-1,3-DIOXOLE)

(71) Applicant: AGC Inc., Chiyoda-ku (JP)

(72) Inventors: Daisuke Jomuta, Tokyo (JP); Yusuke Takahira, Tokyo (JP); Nobuyuki Otozawa, Tokyo (JP); Chikaya Tamitsuji, Tokyo (JP)

(73) Assignee: AGC INC., Tokyo (JP)

( * ) Notice: Subject to any disclaimer, the term of this patent is extended or adjusted under 35 U.S.C. 154(b) by 0 days.

(21) Appl. No.: 16/936,512

(22) Filed: Jul. 23, 2020

(65) Prior Publication Data

US 2020/0354332 A1 Nov. 12, 2020

Related U.S. Application Data

(63) Continuation of application No. PCT/JP2019/003033, filed on Jan. 29, 2019.

(30) Foreign Application Priority Data

Feb. 1, 2018 (JP) .............................. JP2018-016580

(51) Int. Cl.
C07D 317/42 (2006.01)
(52) U.S. Cl.
CPC .................................. C07D 317/42 (2013.01)
(58) Field of Classification Search
CPC .............................. C07D 317/42; C07B 61/00
USPC ....................................................... 549/455
See application file for complete search history.

(56) References Cited

U.S. PATENT DOCUMENTS

| 2,925,424 A | 2/1960 | Simmons, Jr. |
| 3,865,845 A | 2/1975 | Resnick |
| 3,978,030 A | 8/1976 | Resnick |
| 4,393,227 A | 7/1983 | Squire |
| 5,225,576 A | 7/1993 | Navarrini et al. |
| 5,235,074 A | 8/1993 | Navarrini et al. |
| 5,296,617 A | 3/1994 | Navarrini et al. |

FOREIGN PATENT DOCUMENTS

| JP | 06-087848 A | 3/1994 |
| JP | 06-087849 A | 3/1994 |
| JP | 2012-171884 A | 9/2012 |
| WO | WO 03/002501 A1 | 1/2003 |
| WO | WO 2010/128634 A1 | 11/2010 |

OTHER PUBLICATIONS

International Search Report dated Mar. 12, 2019 in PCT/JP2019/003033 filed on Jan. 29, 2019, 2 pages.
Zedda et al., An Improved Synthesis of 2,2-Bis (fluoroxy) perfluoropropane, Inorganic Chemistry vol. 34, No. 22, 1995, pp. 5686-5688.

*Primary Examiner* — Taylor V Oh
(74) *Attorney, Agent, or Firm* — Foley & Lardner LLP

(57) ABSTRACT

The present invention relates to a method for producing a 1,3-dioxolane compound represented by formula 1, the method containing step (a), in which hexafluoroacetone monohydrate is brought into contact with a metal fluoride, step (b), in which fluorine gas is brought into contact, and step (c), in which an olefin compound represented by formula 2 is brought into contact. In formulae 1 and 2, $X^1$ to $X^4$ each independently represent a hydrogen atom, fluorine atom, chlorine atom, or trifluoromethyl group.

[Chem. 1]

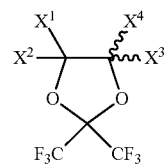

1

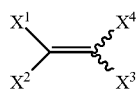

2

10 Claims, No Drawings

PRODUCTION METHODS FOR 1,3-DIOXOLANE COMPOUND AND PERFLUORO(2,2-DIMETHYL-1,3-DIOXOLE)

TECHNICAL FIELD

The present invention relates to novel methods for producing a 1,3-dioxolane compound and perfluoro(2,2-dimethyl-1,3-dioxole).

BACKGROUND ART

Perfluoro(2,2-dimethyl-1,3-dioxole) (PDD) is very useful as a raw material monomer for a functional fluororesin. As described in Patent Literature 1, a 1,3-dioxolane compound to be a precursor of PDD has been conventionally synthesized in multiple stages via halogenation at 4,5-positions after a 1,3-dioxolane skeleton is constructed by using hexafluoroacetone as a starting material.

BACKGROUND ART

Patent Literature

Patent Literature 1: U.S. Pat. No. 2,925,424

SUMMARY OF INVENTION

Problems to be Solved by the Invention

However, since a 1,3-dioxolane is synthesized in multiple stages, the synthesis method described in Patent Literature 1 has a problem that it takes much cost and labor and generates a large amount of waste such as by-products.

Accordingly, it is an object of the present invention to provide a novel method for producing a 1,3-dioxolane compound to be a precursor of PDD, which can easily produce the compound in a small number of steps and is excellent in yield. Moreover, it is also an object to provide a novel method for producing PDD by using the production method.

Means for Solving the Problems

In order to achieve the above-described objects, the present inventors have made various studies on a production method using hexafluoroacetone monohydrate as a starting material. However, since 2,2-bis(fluorooxy)hexafluoropropane in which hexafluoroacetone monohydrate is perfluorinated is a very unstable compound, and in view of such a fact that the yield at the time of using a conventional synthetic method is only 5%, it has been believed difficult to solve the above-described problem (see, Journal of the American Chemical Society 89 (10) 2263-2267 (1967)).

Then, the present inventors have found that the desired 1,3-dioxolane compound can be synthesized in one pot and the 1,3-dioxolane compound can be obtained in high yield when reacting hexafluoroacetone monohydrate with a metal fluoride to effect alkoxylation, then reacting the resultant with fluorine gas to achieve fluoroxylation (—OF formation), and directly adding an olefin compound into the same reaction system. Based thereon, they have accomplished the present invention. Also, the present inventors have been found that the step of reacting the fluorine gas and the step of charging the olefin compound can be interchanged or performed simultaneously.

That is, the present invention relates to the following [1] to [10].

[1] A method for producing a 1,3-dioxolane compound represented by the following formula 1, containing the following step (a) to step (c):

Step (a): a step of bringing hexafluoroacetone monohydrate into contact with a metal fluoride, Step (b): a step of bringing a fluorine gas into contact, and Step (c): a step of bringing an olefin compound represented by the following formula 2 into contact.

[Chem. 1]

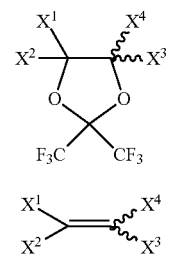

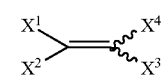

In the formulas 1 and 2, $X^1$ to $X^4$ are each independently a hydrogen atom, a fluorine atom, a chlorine atom, or a trifluoromethyl group.

[2] The method for producing a 1,3-dioxolane compound according to [1], containing using cesium fluoride, potassium fluoride or sodium fluoride as the metal fluoride in the step (a).

[3] The method for producing a 1,3-dioxolane compound according to [1] or [2], containing setting a reaction temperature in the step (b) to −196 to 0° C.

[4] The method for producing a 1,3-dioxolane compound according to any one of [1] to [3], containing using a fluorine gas diluted to 0.1 to 50% by volume as the fluorine gas in the step (b).

[5] The method for producing a 1,3-dioxolane compound according to any one of [1] to [4], in which at least one of $X^1$ and $X^2$ and at least one of $X^3$ and $X^4$ of the olefin compound represented by the formula 2 are both fluorine atoms.

[6] The method for producing a 1,3-dioxolane compound according to any one of [1] to [5], in which the olefin compound represented by the formula 2 is one or more selected from the group consisting of 1,2-dichloro-1,2-difluoroethylene, 1,1,2-trifluoroethylene, tetrafluoroethylene, chlorotrifluoroethylene, hexafluoropropylene, and 1,2-difluoroethylene.

[7] The method for producing a 1,3-dioxolane compound according to any one of [1] to [6], in which the steps (a), (b) and (c) are performed in this order.

[8] A method for producing perfluoro(2,2-dimethyl-1,3-dioxole) represented by the following formula 3, containing the following steps (a), (b), (c)', and (d):

Step (a): a step of bringing hexafluoroacetone monohydrate into contact with a metal fluoride, Step (b): a step of bringing a fluorine gas into contact, Step (c)': a step of bringing an olefin compound represented by the following formula 2' into contact, and Step (d): a step of eliminating $X^1$ and $X^3$ in the following formula 1'.

[Chem. 2]

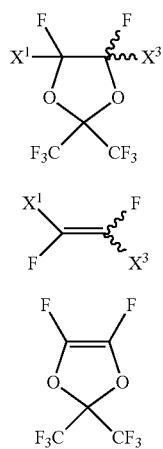

In the formulas 1' and 2', $X^1$ and $X^3$ are each independently a hydrogen atom, a fluorine atom, a chlorine atom, or a trifluoromethyl group.

[9] The method for producing perfluoro(2,2-dimethyl-1,3-dioxole) according to [8], in which the olefin compound represented by the formula 2' is one or more selected from the group consisting of 1,2-dichloro-1,2-difluoroethylene, 1,1,2-trifluoroethylene, tetrafluoroethylene, chlorotrifluoroethylene, hexafluoropropylene, and 1,2-difluoroethylene.

[10] The method for producing perfluoro (2,2-dimethyl-1,3-dioxole) according to [8] or [9], in which the steps (a), (b), (c)', and (d) are performed in this order.

Advantageous Effects of Invention

According to the present invention, perfluoro(2,2-dimethyl-1,3-dioxole), which is very useful as a raw material monomer for a fluororesin, and a 1,3-dioxolane compound to be a precursor thereof can be obtained in a small number of steps and in high yields.

MODES FOR CARRYING OUT THE INVENTION

Hereinafter, the present invention will be described in detail, but the present invention is not limited to the following embodiments, and can be carried out with arbitrary modification in the range without departing from the gist of the present invention.

A wavy line in the structural formulas means that the compound is one of E/Z isomers or a mixture of both thereof.

The production method according to the present invention includes the following steps (a) to (c), and a 1,3-dioxolane compound represented by the following formula 1 can be obtained.

Step (a): a step of bringing hexafluoroacetone monohydrate into contact with a metal fluoride, Step (b): a step of bringing a fluorine gas into contact, and Step (c): a step of bringing an olefin compound represented by the following formula 2 into contact.

[Chem. 3]

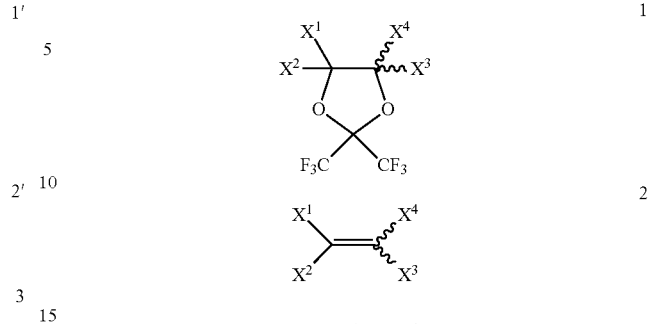

In the formulas 1 and 2, $X^1$ to $X^4$ are each independently a hydrogen atom, a fluorine atom, a chlorine atom, or a trifluoromethyl group.

<Step (a)>

The hexafluoroacetone monohydrate ($HFA \cdot H_2O$) to be used in the step (a) can be obtained, for example, by dehydrating commercially available hexafluoroacetone trihydrate ($HFA \cdot 3H_2O$).

$HFA \cdot H_2O$ is an unstable compound, and is disproportionated to hexafluoroacetone (HFA) and $HFA \cdot 3H_2O$ by the action of moisture in the atmosphere. Also, because of its deliquescence, $HFA \cdot H_2O$ easily changes to $HFA \cdot 3H_2O$. The dehydration treatment of $HFA \cdot 3H_2O$ can be performed by using, for example, calcium chloride as a dehydrating agent and, for example, methylene chloride as a solvent.

In the case where the dehydration treatment is performed by using calcium chloride as the dehydrating agent and methylene chloride as the solvent, calcium chloride is used in an amount of preferably 1 to 10 equivalents and more preferably 1 to 2 equivalents relative to $HFA \cdot 3H_2O$, stirring is conducted for preferably 0.1 to 24 hours and more preferably 0.5 to 6 hours in the presence of methylene chloride. When filtering off the dehydrating agent and concentrating the filtrate, crystals of $HFA \cdot H_2O$ can be obtained.

The dehydrating agent, solvent and method to be used for the dehydrating treatment are not particularly limited to the above-described dehydrating agent, solvent and method as long as $HFA \cdot H_2O$ can be obtained In the step (a), $HFA \cdot H_2O$ and a metal fluoride (MF) are charged into a metal vessel, and both are brought into contact with each other to perform alkoxylation. Since the alkoxylation is an equilibrium reaction, the equilibrium is made shifted to the right side (alkoxide side) in the following scheme.

[Chem. 4]

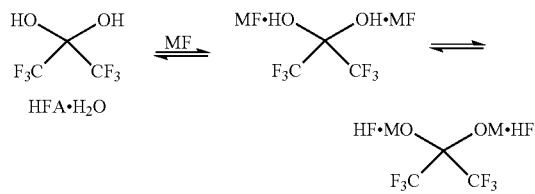

As the metal fluoride, use can be made of cesium fluoride, potassium fluoride, sodium fluoride, or the like. From the viewpoint of reactivity, cesium fluoride or potassium fluoride is preferably used, and cesium fluoride is more preferable.

Furthermore, the metal fluoride is preferably added in an excess amount relative to $HFA \cdot H_2O$, and the addition amount is preferably 2 equivalents or more and more preferably 40 equivalents or more relative to 1 equivalent of HFA.H₂O. The upper limit is not particularly limited, but is generally 100 equivalents.

The alkoxylation may be carried out in the presence of a solvent, and examples of the solvent include halogen solvents containing a halogen atom, and the like. Preferred examples of the halogen solvents include chlorofluoroethers (1,2-dichloro-1,1,2,3,3-pentafluoro-3-[2-chloro-1,1,2,2-tetrafluoroethoxy]-propane, etc.), chlorofluoroalkanes (dichloropentafluoropropane, trichlorotrifluoropropane, etc.), hydrofluoroethers (1,1,2,2-tetrafluoroethyl-2,2,2-trifluoroethyl ether, etc.), polyfluoroalkanes (1,1,1,2,2,3,3,4,4,5,5,6,6-tridecafluorohexane, 1,1,1,2,2,3,3,4,4,5,5,6,6-tridecafluorooctane, etc.), chloroform, methylene chloride, carbon tetrachloride, and the like. Chlorofluoroethers and chlorofluoroalkanes which hardly react with fluorine gas in the fluoroxylation in the step (b) are more preferable. It is also preferable to carry out the reaction without solvent.

HFA.H₂O liquefies at about 45° C. Therefore, it is preferable to carry out the alkoxylation by stirring under a heating condition of 45° C. or higher because the contact with the metal fluoride increases and the reaction ratio enhances. Since HFA.H₂O decomposes at a high temperature, the reaction temperature is more preferably 45° C. to 60° C. for example.

The reaction time is preferably 10 minutes or longer and more preferably 1 hour or longer. The upper limit is not particularly limited, but 12 hours is preferable.

The reaction pressure is preferably 1 MPa or less, more preferably 0.5 MPa or less, further preferably 0.2 MPa or less, and particularly preferably 0 MPa (atmospheric pressure) in gauge pressure.

<Step (b)>

In the step (b), subsequently to the step (a), a fluorine gas is introduced into the metal vessel. That is, by bringing the alkoxylated HFA.H₂O into contact with the fluorine gas, fluoroxylation (—OF formation) shown in the following scheme can be performed to obtain 2,2-bis(fluorooxy)hexafluoropropane.

Moreover, the step (b) (the step of bringing fluorine gas into contact) may be performed after the step (c) to be mentioned later is performed in advance. In this case, the 1,3-dioxolane compound represented by the formula 1 can be obtained by the step (b) subsequent to the step (c). Furthermore, the present step (b) and the step (c) to be mentioned later may be performed simultaneously. Also in this case, the 1,3-dioxolane compound represented by the formula 1 can be obtained.

[Chem. 5]

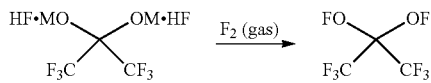

A diluted gas is preferably used as the fluorine gas from the viewpoint of safety and the possibility that the decomposition of the intermediate can be suppressed and the results such as yield and purity may be improved. For example, a fluorine gas diluted to 0.1 to 50% by volume is preferably used, and a fluorine gas diluted to 5 to 20% by volume is more preferably used. Examples of the inert gas to be used for dilution include nitrogen gas, argon gas and the like, and nitrogen gas is preferable from the viewpoint of price and availability.

The fluorine gas is preferably added in an excessive amount relative to the alkoxylated HFA.H₂O since the contact efficiency with the alkoxylated HFA.H₂O is improved and the above-described reaction proceeds. The amount of the fluorine gas to be added is preferably 2 equivalents or more and more preferably 5.5 equivalents or more relative to 1 equivalent of the alkoxylated HFA.H₂O. The upper limit is not particularly limited, but is generally 10 equivalents.

At the time when fluorine gas is introduced to carry out fluoroxylation, the inside of the metal vessel is preferably pressurized with the fluorine gas. The pressure at that time is preferably 3 MPa or less, more preferably 1 MPa or less and further preferably 0.5 MPa or less in gauge pressure. It is also preferable to supplementarily add the fluorine gas when the fluorine gas is consumed and the pressure drops due to the progress of the fluoroxylation. Furthermore, the fluorine gas may be made to flow in the metal vessel.

In the case where the diluted fluorine gas is used, the charge amount (equivalent amount) is determined in terms of 100% by volume fluorine gas.

Since 2,2-bis(fluoroxy)hexafluoropropane obtained in the step (b) is very unstable, the fluoroxylation is preferably carried out at a low temperature. Specifically, it is carried out preferably at 0° C. or lower, more preferably at −40° C. or lower and further preferably at −75° C. or lower. The lower limit is, for example, −196° C., and liquid nitrogen can be used as a refrigerant.

The lower limit of the reaction time is not particularly limited as long as reaction conversion occurs, and is, for example, preferably 30 minutes, more preferably 3 hours, and further preferably 6 hours. The upper limit is not particularly limited as long as the product does not decompose, but is, for example, preferably 12 hours.

<Step (c)>

After the step (b), the fluorine gas or the fluorine gas and the inert gas remaining in the metal vessel are purged, that is, exhausted (released) to the outside of the metal vessel, and the olefin compound represented by the following formula 2 is added to the metal vessel and brought into contact to carry out the olefin addition shown in the following scheme, to thereby obtain the 1,3-dioxolane compound represented by the following formula 1.

Also, after the step (a) mentioned above, the present step (c) (the step of bringing the olefin compound represented by the following formula 2 into contact) may be performed, and then the step (b) mentioned above may be performed. Furthermore, the present step (c) and the aforementioned step (b) may be performed simultaneously. In this case, also, the 1,3-dioxolane compound represented by the formula 1 can be obtained.

[Chem. 6]

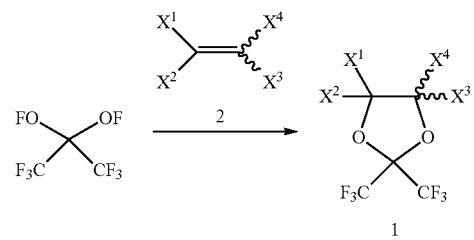

1

In the above-mentioned formulas 1 and 2, $X^1$ to $X^4$ are each independently a hydrogen atom, a fluorine atom, a chlorine atom, or a trifluoromethyl group.

The olefin compound represented by the formula 2 in which at least one of $X^1$ and $X^2$ and at least one of $X^3$ and $X^4$ are both fluorine atoms is preferable since perfluoro(2,2-dimethyl-1,3-dioxole) (PDD) obtained from the 1,3-dioxolane compound represented by the formula 1 is useful as a raw material monomer for a fluororesin.

More specifically, preferable examples of the olefin compound represented by the formula 2 include 1,2-dichloro-1,2-difluoroethylene (R1112), 1,1,2-trifluoroethylene (R1123), tetrafluoroethylene (TFE), chlorotrifluoroethylene (CTFE), hexafluoropropylene (HFP), 1,2-difluoroethylene, 1-chloro-1,2-difluoroethylene, and the like. These olefin compounds may be used alone or in combination of two or more thereof, but using one compound alone is preferable. As the olefin compound represented by the formula 2, R1112 and R1123 are more preferable, and R1112 is particularly preferable.

The olefin compound represented by the formula 2 has a low boiling point and easily volatilizes depending on its structure. In such a case, the compound is preferably used in the step (c) in a state of being diluted with a solvent.

The solvent is not particularly limited as long as it does not hinder the progress of the above-described olefin addition reaction but, for example, a halogen solvent containing a halogen atom is preferable. Preferred examples of the halogen solvent include chlorofluoroethers (1,2-dichloro-1,1,2,3,3-pentafluoro-3-[2-chloro-1,1,2,2-tetrafluoroethoxy]-propane, etc.), chlorofluoroalkanes (dichloropentafluoropropane, trichlorotrifluoropropane, etc.), hydrofluoroethers (1,1,2,2-tetrafluoroethyl-2,2,2-trifluoroethyl ether, etc.), polyfluoroalkanes (1,1,1,2,2,3,3,4,4,5,5,6,6-tridecafluorohexane, 1,1,1,2,2,3,3,4,4,5,5,6,6-tridecafluorooctane, etc.), chloroform, methylene chloride, carbon tetrachloride, and the like. More preferred are chlorofluoroethers and chlorofluoroalkanes which hardly react with the residual fluorine gas.

Usually, the step (c) is preferably performed at the same reaction temperature as in the step (b). That is, it is preferably performed at a low temperature. Specifically, it is preferably performed at 0° C. or lower, more preferably at −40° C. or lower and further preferably at −75° C. or lower.

The reaction time is preferably 30 minutes or longer and more preferably 1 hour or longer. The upper limit is not particularly limited, but for example, 12 hours is preferable.

The reaction may be carried out under pressure with an inert gas. The reaction pressure is preferably 3 MPa or less, more preferably 1 MPa or less and further preferably 0.5 MPa or less in gauge pressure. Examples of the inert gas to be used include nitrogen gas, argon gas and the like. Nitrogen gas is preferable from the viewpoint of price and availability.

Moreover, the reaction is also preferably carried out under atmospheric pressure.

As described above, the production method according to the present invention is very useful since synthesis can be performed in one pot using a metal vessel in the steps (a) to (c) and the 1,3-dioxolane compound represented by the formula 1 can be obtained in a small number of steps. The steps (a), (b) and (c) are particularly preferably performed in this order.

In the case where geometrical isomers are present for the 1,3-dioxolane compound represented by the formula 1, the 1,3-dioxolane compound is obtained as a mixture of E-form and Z-form. Whereas the conventional synthesis method gives a 1,3-dioxolane compound in a ratio of about E/Z=60/40, the production method according to the present invention gives more amount of E-form in a ratio of E/Z=about 80/20.

In the step (d) mentioned below, in the case where perfluoro(2,2-dimethyl-1,3-dioxole) (PDD) represented by the formula 3 is synthesized by using the dioxolane compound represented by the formula 1' among the 1,3-dioxolane compounds represented by the formula 1, it has been known that PDD is synthesized mainly from the E-form (trans form) among the E/Z isomers of the 1,3-dioxolane compound represented by the formula 1'. In this regard, since the 1,3-dioxolane compound represented by the formula 1' can be obtained in a state that the amount of E-form is large as compared with the case of a conventional method, the production method according to the present invention is very useful also in view of the possibility of a high-yield synthesis of PDD.

<Step (d)>

In the case where the olefin compound represented by the formula 2 in the step (c) is an olefin compound represented by the following formula 2' (step (c)'), the 1,3-dioxolane compound represented by the following formula 1' is obtained after passing through the steps (a), (b) and (c)', and perfluoro(2,2-dimethyl-1,3-dioxole) represented by the following formula 3 can be obtained by eliminating $X^1$ and $X^3$ in the formula 1' in the subsequent step (d).

Here, the steps (a), (b) and (c)' may be performed, similarly to the steps (a) to (c), after the step (a), in the order of the steps (b) and (c)' or in the order of the steps (c)' and (b), or the steps (b) and (c)' may be performed simultaneously. The steps (a), (b), (c)', and (d) are particularly preferably performed in this order.

In the formulas 1' and 2', $X^1$ and $X^3$ are each independently a hydrogen atom, a fluorine atom, a chlorine atom, or a trifluoromethyl group.

[Chem. 7]

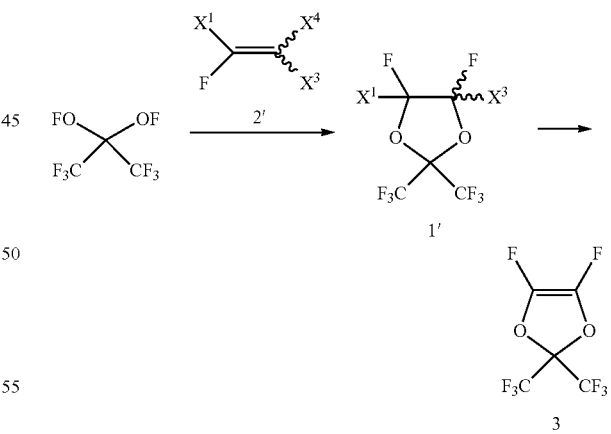

The method of eliminating $X^1$ and $X^3$ in the step (d) can be performed by a known method. The combination of $X^1$ and $X^3$ is preferably a chlorine atom and a chlorine atom, a hydrogen atom and a chlorine atom or a hydrogen atom and a fluorine atom. For example, in the case where both $X^1$ and $X^3$ are chlorine atoms, dechlorination can be achieved by adding the compound represented by the formula 1' dropwise to a heated solvent in the presence of a metal such as Zn or Mg.

The dechlorination solvent is not particularly limited as long as it does not hinder the progress of the reaction, but tetrahydrofuran, 1,4-dioxane and N, N-dimethylformamide are preferable.

Moreover, in the case where $X^1$ and $X^3$ are a hydrogen atom and a chlorine atom or a hydrogen atom and a fluorine atom, for example, $X^1$ and $X^3$ can be eliminated by heating the compound in a solution of sodium hydroxide or potassium hydroxide.

In the compound represented by the formula 2, even in the case where at least one of $X^1$ and $X^2$ and at least one of $X^3$ and $X^4$ are both not fluorine atoms, that is, even in the case where it is not the compound represented by the formula 2', a dioxole compound can be synthesized from the dioxolane compound represented by the formula 1 by using the same method as in the step (d).

The 1,3-dioxolane compound obtained in the step (b) or (c) and the dioxole compound obtained in the step (d) can be identified by a conventionally known method. For example, identification can be performed by $^{19}$F-NMR, GC or GC-MS, and the yield can be determined.

Furthermore, the compounds can be highly purified or isolated by distillation or column chromatography.

EXAMPLES

Hereinafter, the present invention will be specifically described with reference to Examples, but the present invention is not limited thereto. The 20 vol %-$F_2/N_2$ gas means a gas obtained by diluting fluorine gas to 20% by volume by using nitrogen gas as an inert gas.

<Evaluation Method>

In the present Examples, 1,3-dioxolane compounds and perfluoro(2,2-dimethyl-1,3-dioxole) were identified by $^{19}$F-NMR measurement on a nuclear magnetic resonance apparatus (trade name: AL-300) manufactured by JEOL Ltd., and the yield was also determined.

Example 1

To a 0.2 L-metal-made reaction vessel charged with 16.5 g (40 mol equivalents) of cesium fluoride was added 0.5 g (1 mol equivalent) of hexafluoroacetone monohydrate in a diluted state with 60.9 g of CFE419 ($CF_2ClCFClCF_2OCF_2CF_2Cl$). Alkoxylation was carried out by stirring the mixture at room temperature for 12 hours as it was (step (a)). Then, after cooling the metal vessel to −78° C., a 20 vol %-$F_2/N_2$ gas was introduced so as to be 0.2 g (2 mol equivalent) in terms of 100 vol %-$F_2$ gas, followed by aging for 4.7 hours, to perform fluoroxylation (step (b)).

After the residual pressure in the metal vessel was purged while maintaining the temperature of the metal vessel at −78° C., 6.3 g of R1112 (1,2-dichloro-1,2-difluoroethylene, E/Z mixture) was fed in a diluted state with CFE419, followed by aging for 1 hour to perform olefin addition, to thereby obtain the 1,3-dioxolane compound (E/Z form) represented by the following formula 1″ at 11.5% yield (Step (c)). The conversion rate of hexafluoroacetone monohydrate was 91.0%.

PDD represented by the following formula 3 was obtained by dechlorinating the obtained 1,3-dioxolane compound with a metal such as Zn or Mg (step (d)).

[Chem. 8]

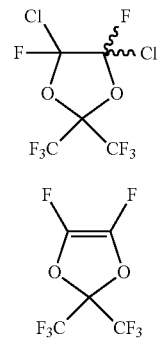

Example 2

The 1,3-dioxolane compound (E/Z form) represented by the above-mentioned formula 1″ was obtained in 27.9% yield in the same manner as in Example 1 except that the 20 vol % $F_2/N_2$ gas in the fluoroxylation in the step (b) was introduced so as to be 0.57 g (5.5 mol equivalents) in terms of 100 vol %-$F_2$ gas, the aging time was changed to 6.7 hours, and the amount of R1112 in the olefin addition in the step (c) was changed to 20 g. Then, PDD represented by the above-mentioned formula 3 was obtained in the same manner as in Example 1.

Example 3

The 1,3-dioxolane compound (E/Z form) represented by the above-mentioned formula 1″ was obtained in 10.1% yield in the same manner as in Example 1 except that 6.3 g (40 mol equivalents) of potassium fluoride was used instead of cesium fluoride in the alkoxylation in the step (a), alkoxylation was carried out by stirring the mixture at 50° C. for one hour without using a solvent, the aging time was changed to 4 hours in the fluoroxylation in the step (b), and the amount of R1112 in the olefin addition in the step (c) was changed to 4.7 g. Then, PDD represented by the above-mentioned formula 3 was obtained in the same manner as in Example 1.

Example 4

The 1,3-dioxolane compound (E/Z form) represented by the above-mentioned formula 1″ was obtained in 14.8% yield in the same manner as in Example 3 except that 16.5 g (40 mol equivalents) of cesium fluoride was used instead of potassium fluoride in the alkoxylation in the step (a) and the aging temperature was changed to −40° C. in the fluoroxylation in the step (b). Then, PDD represented by the above-mentioned formula 3 was obtained in the same manner as in Example 1.

Example 5

The 1,3-dioxolane compound (E/Z form) represented by the above-mentioned formula 1″ was obtained in 36.0% yield in the same manner as in Example 4 except that the aging temperature was changed to −78° C. and the aging time was changed to 4.1 hours in the fluoroxylation in the step (b), and the amount of R1112 in the olefin addition in the step (c) was changed to 5.8 g. Then, PDD represented by the above-mentioned formula 3 was obtained in the same manner as in Example 1.

Example 6

The 1,3-dioxolane compound (E/Z form) represented by the above-mentioned formula 1" was obtained in 48.3% yield in the same manner as in Example 5 except that the 20 vol %-$F_2/N_2$ gas in the fluoroxylation in the step (b) was introduced so as to be 0.57 g (5.5 mol equivalents) in terms of 100 vol %-$F_2$ gas, the aging time was changed to 6 hours, and the amount of R1112 in the olefin addition in the step (c) was changed to 14.6 g. Then, PDD represented by the above-mentioned formula 3 was obtained in the same manner as in Example 1.

Example 7

The 1,3-dioxolane compound represented by the following formula 1''' was obtained in 6.9% yield in the same manner as in Example 4 except that 1.1 g of R1123 (1,1,2-trifluoroethylene) was used instead of R1112 in the olefin addition in the step (c).

[Chem. 9]

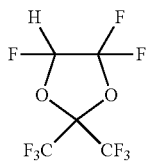

1'''

Example 8

The 1,3-dioxolane compound (E/Z form) represented by the above-mentioned formula 1" was obtained in 4.3% yield in the same manner as in Example 1 except that 6.2 g (15 mol equivalents) of cesium fluoride was used in the alkoxylation in the step (a). Then, PDD represented by the above-mentioned formula 3 was obtained in the same manner as in Example 1.

Example 9

The 1,3-dioxolane compound (E/Z form) represented by the above-mentioned formula 1" was obtained in 0.6% yield in the same manner as in Example 1 except that 0.8 g (2 mol equivalents) of cesium fluoride was used in the alkoxylation in the step (a). Then, PDD represented by the above-mentioned formula 3 was obtained in the same manner as in Example 1.

Example 10

The 1,3-dioxolane compound (E/Z form) represented by the above-mentioned formula 1" was obtained in 9.6% yield in the same manner as in Example 1 except that a 5 vol %-$F_2/N_2$ gas as the $F_2/N_2$ gas volume in the fluoroxylation in the step (b) was introduced so as to be 0.57 g (5.5 mol equivalents) in terms of 100 vol %-$F_2$ gas and the aging time was changed to 25 hours. Then, PDD represented by the above-mentioned formula 3 was obtained in the same manner as in Example 1.

Example 11

The 1,3-dioxolane compound (E/Z form) represented by the above-mentioned formula 1" was obtained in 36% yield in the same manner as in Example 1 except that a 50 vol %-$F_2/N_2$ gas as the $F_2/N_2$ gas volume in the fluoroxylation in the step (b) was introduced so as to be 0.57 g (5.5 mol equivalents) in terms of 100 vol %-$F_2$ gas and the aging time was changed to 6 hours. Then, PDD represented by the above-mentioned formula 3 was obtained in the same manner as in Example 1.

Example 12

The 1,3-dioxolane compound (E/Z form) represented by the above-mentioned formula 1" was obtained in 4.4% yield in the same manner as in Example 4 except that the aging temperature was changed to −10° C. and the aging time was changed to 4.1 hours in the fluoroxylation in the step (b), and the amount of R1112 in the olefin addition in the step (c) was changed to 5.8 g. Then, PDD represented by the above-mentioned formula 3 was obtained in the same manner as in Example 1.

While the present invention has been described in detail and with reference to specific embodiments thereof, it will be apparent to one skilled in the art that various changes and modifications can be made therein without departing from the spirit and scope thereof. The present application is based on Japanese Patent Application (No. 2018-016580) filed on Feb. 1, 2018, and the contents thereof are incorporated herein by reference.

INDUSTRIAL APPLICABILITY

According to the present invention, a 1,3-dioxolane compound to be a precursor of perfluoro (2,2-dimethyl-1,3-dioxole) (PDD) can be obtained in a small number of steps and in high yields. A polymer using subsequently obtained PDD as a raw material monomer for a fluororesin is expected to be utilized in a variety of fields of coating films and optical materials.

The invention claimed is:
1. A method for producing a 1,3-dioxolane compound represented by the following formula 1, containing the following step (a) to step (c):
   step (a): a step of bringing hexafluoroacetone monohydrate into contact with a metal fluoride,
   step (b): a step of bringing a fluorine gas into contact, and
   step (c): a step of bringing an olefin compound represented by the following formula 2 into contact,

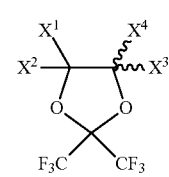

1

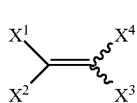

in the formulas 1 and 2, $X^1$ to $X^4$ are each independently a hydrogen atom, a fluorine atom, a chlorine atom, or a trifluoromethyl group.

2. The method for producing a 1,3-dioxolane compound according to claim 1, comprising using cesium fluoride, potassium fluoride or sodium fluoride as the metal fluoride in the step (a).

3. The method for producing a 1,3-dioxolane compound according to claim 1, comprising setting a reaction temperature in the step (b) to −196 to 0° C.

4. The method for producing a 1,3-dioxolane compound according to claim 1, comprising using a fluorine gas diluted to 0.1 to 50% by volume as the fluorine gas in the step (b).

5. The method for producing a 1,3-dioxolane compound according to claim 1, wherein at least one of $X^1$ and $X^2$ and at least one of $X^3$ and $X^4$ of the olefin compound represented by the formula 2 are both fluorine atoms.

6. The method for producing a 1,3-dioxolane compound according to claim 1, wherein the olefin compound represented by the formula 2 is one or more selected from the group consisting of 1,2-dichloro-1,2-difluoroethylene, 1,1,2-trifluoroethylene, tetrafluoroethylene, chlorotrifluoroethylene, hexafluoropropylene, and 1,2-difluoroethylene.

7. The method for producing a 1,3-dioxolane compound according to claim 1, wherein the steps (a), (b) and (c) are performed in this order.

8. A method for producing perfluoro(2,2-dimethyl-1,3-dioxole) represented by the following formula 3, comprising the following steps (a), (b), (c)', and (d):
step (a): a step of bringing hexafluoroacetone monohydrate into contact with a metal fluoride,
step (b): a step of bringing a fluorine gas into contact,
step (c)': a step of bringing an olefin compound represented by the following formula 2' into contact, and
step (d): a step of eliminating $X^1$ and $X^3$ in the following formula 2',

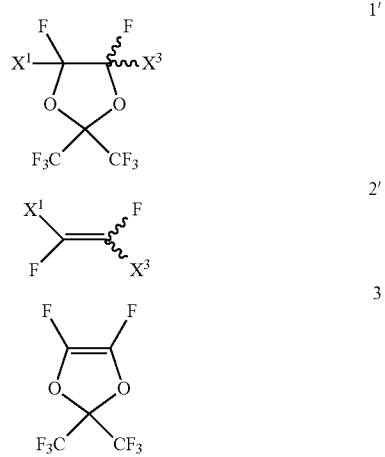

in the formulas 1' and 2', $X^1$ and $X^3$ are each independently a hydrogen atom, a fluorine atom, a chlorine atom, or a trifluoromethyl group.

9. The method for producing perfluoro(2,2-dimethyl-1,3-dioxole) according to claim 8, wherein the olefin compound represented by the formula 2' is one or more selected from the group consisting of 1,2-dichloro-1,2-difluoroethylene, 1,1,2-trifluoroethylene, tetrafluoroethylene, chlorotrifluoroethylene, hexafluoropropylene, and 1,2-difluoroethylene.

10. The method for producing perfluoro (2,2-dimethyl-1,3-dioxole) according to claim 8, wherein the steps (a), (b), (c)', and (d) are performed in this order.

* * * * *